United States Patent [19]

Rosenberg

[11] Patent Number: 4,634,662
[45] Date of Patent: Jan. 6, 1987

[54] ORTHODONTIC BRACKET HAVING ARCHWIRE SEATING AND LOCKING MECHANISM

[76] Inventor: Farel Rosenberg, 10535 Wilshire Blvd., Los Angeles, Calif. 90024

[21] Appl. No.: 825,452

[22] Filed: Feb. 3, 1986

[51] Int. Cl.$^4$ .............................................. A61C 7/00
[52] U.S. Cl. .................................................... 433/10
[58] Field of Search ........................ 433/10, 11, 13, 16

[56] References Cited

U.S. PATENT DOCUMENTS 4,419,078 12/1983 Pletcher ................................. 433/10
4,559,012 12/1985 Pletcher ................................. 433/10

Primary Examiner—Robert Peshock
Attorney, Agent, or Firm—Gilbert Kivenson

[57] ABSTRACT

An orthodontic bracket with a self-contained seating and locking mechanism which incorporates a slidable, tapered and rotatable plug with an attached lever system. When the plug is rotated, the lever system comes in contact with and seats an archwire contained in the bracket slot. When the plug is then moved laterally, a condition of frictional retention is achieved. The archwire is thus firmly seated and locked in its slot by the lever system. When the plug is next moved in the opposite direction, the archwire is once again freed.

2 Claims, 6 Drawing Figures

ORTHODONTIC BRACKET HAVING ARCHWIRE SEATING AND LOCKING MECHANISM

BACKGROUND OF THE INVENTION

The treatment of malaligned teeth orthodontically involves the use of corrective mechanical forces applied over a period of time to move the teeth into proper orientation. The most frequently used devices are slotted brackets rigidly mounted on the teeth and a preflexed archwire which is placed in each slot and fastened. Under these conditions the spring pressure tending to return the wire to its original form is now exerted on each tooth as a corrective force. The result is a more desirable alignment of the teeth.

Archwires for the correcting of orthodontic problems are normally ligated to slotted brackets. The latter have previously been cemented to the teeth or, in an earlier process, soldered to bands which were then cemented around the teeth. Ligating is done with fine wires which are looped around "tie wings", small projections which are cast into each bracket. Although the method does hold the archwire securely, the handling of the fine ligation wires requires careful manipulation by the orthodontist and a considerable amount of chair time. The ties must also be removed and replaced each time that an orthodontic adjustment is made as the treatment progresses. The ligation wires constitute food traps (in addition to those produced by the archwires) and make the maintenance of hygienic mouth conditions more difficult.

A number of clamping brackets have been invented including those by Pletcher, U.S. Pat. No. 4,077,126 by Fujita, U.S. Pat. No. 4,355,975, and by Brader, U.S. Pat. No. 3,327,393. These devices, while eliminating the need for ligating wires, are themselves complicated and costly to manufacture in the small sizes needed in orthodontics. The brackets of Fujita and Brader utilize removable components which increase the danger of swallowing or inhalation spasms by the patient. In addition, these devices are unable to seat all of the various sizes of archwire into the base of their slots firmly, a condition necessary to maximize the tooth moving capability of the system.

It is an object of the present invention to provide an orthodontic bracket with no readily separable parts.

It is a second objective of the invention to provide a simple construction which permits relatively low cost fabrication.

It is a third and most important object of the invention to fully seat and lock various sizes and shapes of archwires and thereby maximize the tooth moving capability of the archwire system.

These and other objectives will become clear in the detailed description which follows.

SUMMARY OF THE INVENTION

This invention relates to an orthodontic bracket with provision for full archwire seating and locking. The mechanism for seating and locking includes a tapered plug installed within a matching, tapered cylindrical cavity. A lever is attached to the plug. The lever rests at its other end on the archwire or on a spring which then contacts the archwire. When the plug is rotated so as to press the lever or spring against the archwire (seating it) while simultaneously forcing the tapered plug into its cavity (locking it), the frictional adhesion between plug and cavity prevents loosening of the archwire in the bracket slot. Applying a lateral force to the opposite end of the tapered plug will cause it to move out of contact with the cavity, break its adhesion, turn, and release the seated, locked archwire.

DESCRIPTION OF THE INVENTION

Figure 1:
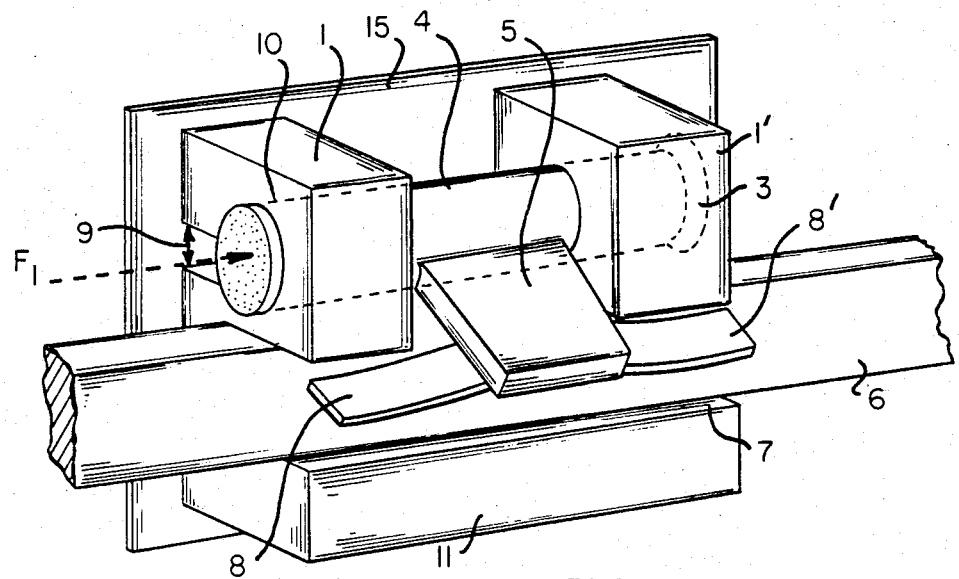
FIG. 1 is an isometric view of one embodiment of the invention showing the unlocked archwire in its slot.
Figure 2:
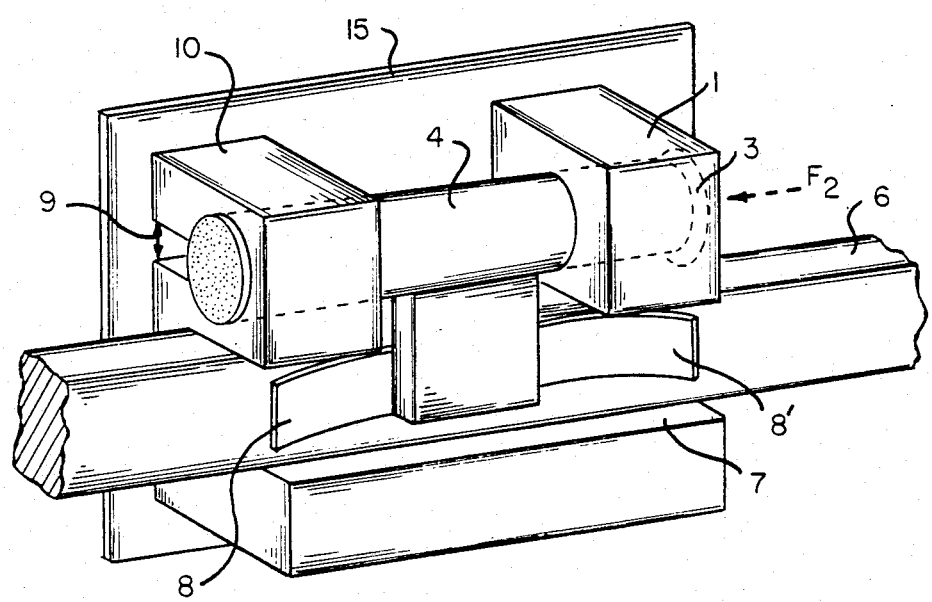
FIG. 2 is an isometric view of the embodiment of FIG. 1 with the archwire fully seated and locked.
Figure 3:
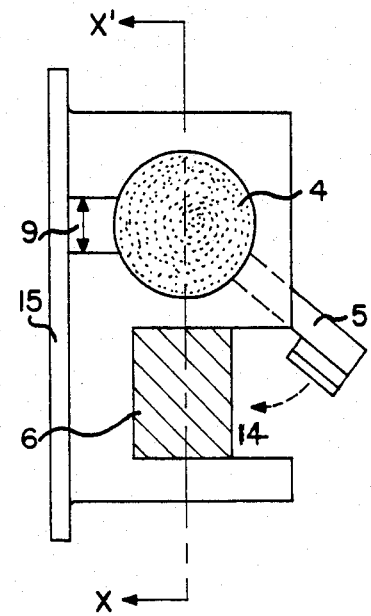
FIG. 3 is an end view of the embodiment of FIG. 1.
Figure 4:
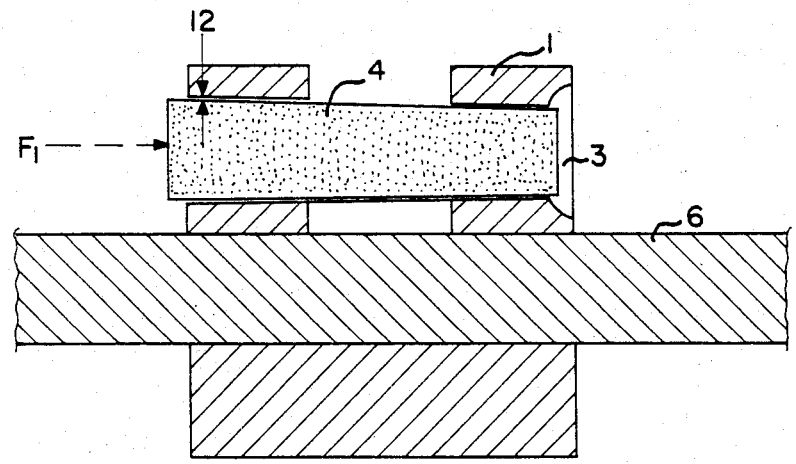
FIG. 4 is a cross-section taken along X—X' of FIG. 3.

An orthodontic bracket with provision for archwire seating and locking is shown in FIGS. 1 and 2. The bracket's upper portion is milled vertically in the center creating left and right members 1 and 1'. The bracket is also milled horizontally at 7 in its front surface to receive an archwire 6. A horizontal, cylindrical, and tapered cavity 10, is cut in members 1 and 1' to receive a tapered plug 4 to which a lever 5 is rigidly mounted. Lever 5 terminates in the flat springs 8 and 8' which can be made to bear on and seat the archwire by clockwise rotation of the plug—arc 14 in FIG. 3. The plug has a clearance 12 (FIG. 4) with its cavity when it is in the unlocked position. The plug may be roughened along its contact surface or made by various sintered metal casting techniques or constructed of plastics to produce the desired frictional adhesion with the surfaces of the cavity.

The slot 9 (FIGS. 1, 2 and 3) in the bracket permits the assembly of plug, lever and springs to be inserted into the rear of the body of the bracket and rotated into operating position. A bonding base 15 is then attached to the rear of the bracket, thus sealing in the operating mechanism.

In operation of the bracket after it is tooth mounted, the plug is rotated counter-clockwise so that the lever and spring is in the open position. The plug can be temporarily held in this position by applying a slight force in the direction $F_1$, FIG. 4. The archwire 6 is then placed in its slot; the plug is then released by a force in the direction $F_2$ and rotated clockwise until the springs seat the archwire against the bottom of the slot. A strong force is simultaneously applied in the direction $F_1$ to lock the plug into the cavity and to lock the archwire into the slot.

To unlock the archwire a force is applied in the direction $F_2$ which breaks the frictional adhesion between plug and cavity. Stored spring forces acting through lever 5 rotate the plug and thus release the archwire. The recess 3 (FIGS. 4 and 5) facilitates contact of the force-applying instrument with the smaller end of the plug. The lever 5 can be temporarily locked again in an open position by applying force in the direction $F_1$ to make more convenient the removal, readjustment and reinsertion of the archwire in a series of brackets on adjacent teeth.

Figure 5:
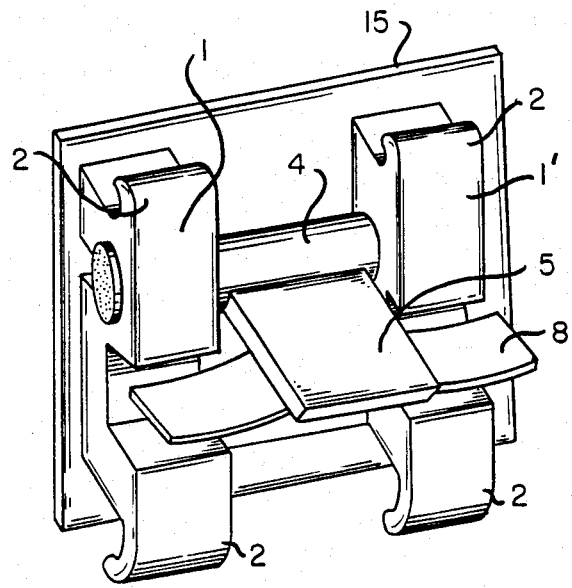
FIG. 5 is an isometric view of a second embodiment of the invention which includes tie wings and twin construction.

In a second embodiment of the invention shown in FIG. 5, tie wings 2 have been incorporated to permit conventional ligating wires to be used in these cases where extreme malpositioning of the teeth initially requires them.

Figure 6:
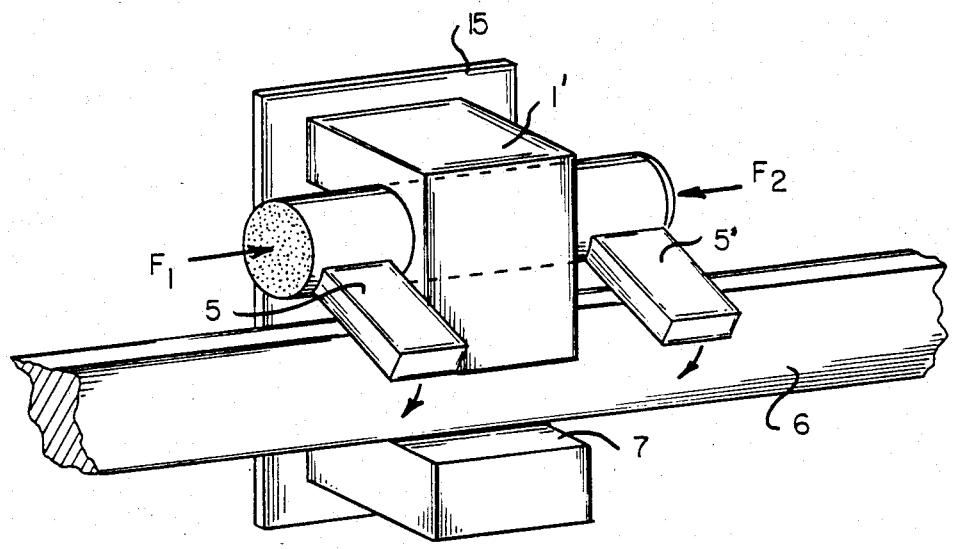
FIG. 6 is an isometric view of a third embodiment of the invention.

A third embodiment of the invention is shown in FIG. 6. A single block is used with levers 5 and 5' at either end of the plug 4. The levers contact the archwire directly in this case. The method of locking and unlocking the plug by the use of forces in the directions $F_1$ and $F_2$ is the same. With this embodiment it is possible to vary the angular spacing of the levers 5 and 5' with respect to the plug 4 so that a slot of varying depth can be used. In this case orthodontic tooth rotation will be produced by the bracket.

What is claimed is:

1. An in a second embodiment:
   (a) A block containing a tapered cylindrical cavity to accommodate a cylindrical, tapered plug and provided with a first rectangular, horizontal slot cut into its front surface to hold an archwire and provided with a second horizontal slot cut into its rear surface communicating along its length with said two piece cylindrical cavity and provided with a vertical slot intersecting the cylindrical cavity and both horizontal slots, said vertical slot dividing the cylindrical cavity into two portions;
   (b) a cylindrical, tapered plug which is rotatably and slidably mounted in said cylindrical cavity;
   (c) a lever attached to and extending radially from said plug, terminating in leaf springs which can be brought to bear and seat an archwire placed in the first rectangular slot, said lever, leaf springs and plug being a pre-assembly which can be brought into the cylindrical cavity through said second horizontal slot;
   (d) a bonding base joined to the rear surface of the block after assembly to serve as an attachment surface to a tooth;
   whereby rotation of the plug causes the lever and springs to exert pressure on the archwire, and simultaneously forcing the plug laterally into frictional contact with the tapered cylindrical cavity seats the archwire to the bottom of its slot and locks it; conversely, forcing the plug out of contact with the two piece tapered cylindrical cavity unlocks the archwire to permit its removal.

2. An orthodontic bracket comprised of:
   (a) a block containing a horizontal, tapered, cylindrical cavity to accommodate a cylindrical tapered plug and provided with a first rectangular horizontal slot cut into its front surface to hold an archwire and provided with a second horizontal slot cut into its rear surface and communicating along its length with said cylindrical cavity;
   (b) a cylindrical, tapered plug which is rotatably and slidably mounted in said cylindrical cavity and which is of a length to protrude past both ends of the cavity;
   (c) a lever attached at each protruding end of the plug and of a length to bear on and anchor an archwire placed in said first horizontal slot, said levers and plug being a pre-assembly which can be brought into the cylindrical cavity through said second horizontal slot;
   (d) a cylindrical, tapered plug which is rotatably and slidably mounted in said cylindrical cavity and which is of a length to protrude past both ends of the cavity;
   (e) a bonding base joined to the rear surface of the block after adding said pre-assembly to serve as an attachment area to a tooth;
   whereby rotation of the plug laterally into frictional contact with the tapered cylindrical cavity seats and locks the archwire to the base of its slot, while forcing the plug out of contact with the tapered cylindrical cavity unclamps the archwire and permits it to be removed.

* * * * *